United States Patent
Tomita et al.

(10) Patent No.: US 8,639,320 B2
(45) Date of Patent: Jan. 28, 2014

(54) MUSCLE-ACTIVITY DIAGNOSIS APPARATUS, METHOD, AND PROGRAM

(75) Inventors: Takashi Tomita, Kanagawa (JP); Akane Sano, Tokyo (JP); Haruo Oba, Kanagawa (JP)

(73) Assignee: Sony Corporation, Tokyo (JP)

( * ) Notice: Subject to any disclaimer, the term of this patent is extended or adjusted under 35 U.S.C. 154(b) by 154 days.

(21) Appl. No.: 13/152,564

(22) Filed: Jun. 3, 2011

(65) Prior Publication Data

US 2011/0313310 A1   Dec. 22, 2011

(30) Foreign Application Priority Data

Jun. 16, 2010   (JP) ................. P2010-137099

(51) Int. Cl.
*A61B 5/04* (2006.01)
*A61B 5/0408* (2006.01)
*A61B 5/042* (2006.01)

(52) U.S. Cl.
USPC ............ 600/546; 600/544; 600/545; 600/547

(58) Field of Classification Search
USPC .......... 600/300, 544, 545, 546, 547, 586, 595
See application file for complete search history.

(56) References Cited

U.S. PATENT DOCUMENTS

| | | | | |
|---|---|---|---|---|
| 4,919,143 A * | 4/1990 | Ayers | ............................. | 600/545 |
| 5,024,235 A * | 6/1991 | Ayers | ............................. | 600/545 |
| 5,497,781 A * | 3/1996 | Chen et al. | ................... | 600/546 |
| 5,794,203 A * | 8/1998 | Kehoe | ............................ | 704/271 |
| 7,558,622 B2 * | 7/2009 | Tran | ............................... | 600/509 |
| 7,733,224 B2 * | 6/2010 | Tran | ............................... | 340/540 |
| 8,082,149 B2 * | 12/2011 | Schultz et al. | ................ | 704/235 |
| 8,108,036 B2 * | 1/2012 | Tran | ............................... | 600/509 |
| 2007/0276270 A1 * | 11/2007 | Tran | ............................. | 600/508 |
| 2007/0276281 A1 * | 11/2007 | Sarkela | ......................... | 600/546 |
| 2008/0103769 A1 * | 5/2008 | Schultz et al. | ................ | 704/235 |
| 2009/0318779 A1 * | 12/2009 | Tran | ............................. | 600/301 |
| 2012/0092157 A1 * | 4/2012 | Tran | ......................... | 340/539.12 |

FOREIGN PATENT DOCUMENTS

| | | |
|---|---|---|
| JP | 63-172322 | 7/1988 |
| JP | 1-86936 | 3/1989 |
| JP | 10-143309 | 5/1998 |
| JP | 2000-285221 | 10/2000 |
| JP | 3983989 | 7/2007 |
| JP | 2008-67911 | 3/2008 |

* cited by examiner

*Primary Examiner* — Sean Dougherty
(74) *Attorney, Agent, or Firm* — K&L Gates LLP

(57) ABSTRACT

A muscle-activity diagnosis apparatus includes: an acquiring section acquiring a myoelectric signal from a test subject; using the myoelectric signal as an original signal, a transformed-signal generating section generating a transformed signal by performing Hilbert transformation and inverse Fourier transformation on the original signal; a phase-velocity calculation section calculating a phase velocity of the myoelectric signal on the basis of phases of the original signal and the transformed signal; and on the basis of a plurality of feature quantities of a waveform of the myoelectric signal in a unit time and the plurality of feature quantities including at least a size of amplitude of the myoelectric signal and the calculated phase velocity, a state-identifying section identifying an activity state of a muscle of a predetermined part of a body of the test subject for each of the unit time.

8 Claims, 13 Drawing Sheets

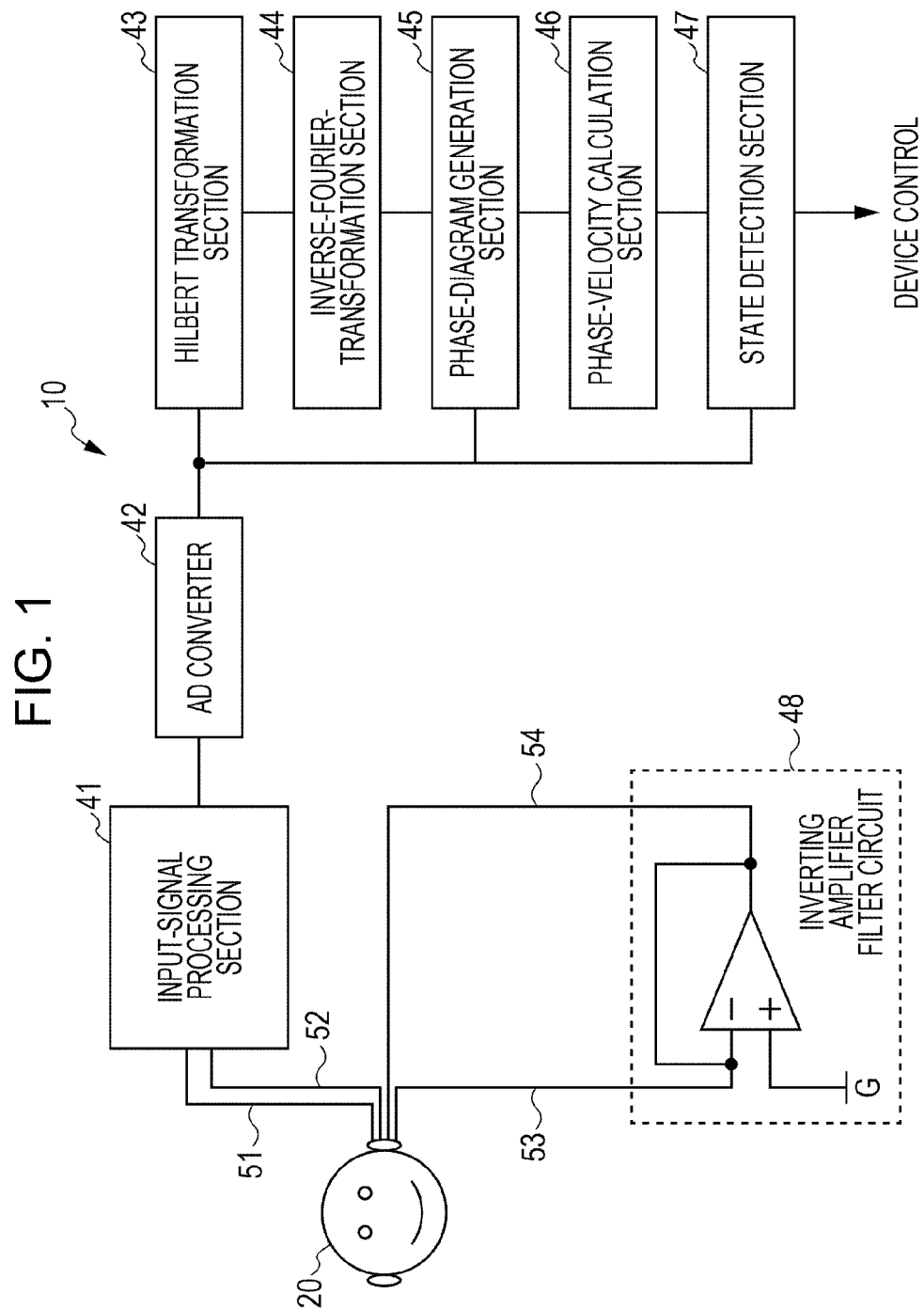

MUSCLE-ACTIVITY DIAGNOSIS APPARATUS, METHOD, AND PROGRAM

CROSS REFERENCES TO RELATED APPLICATIONS

The present application claims priority to Japanese Priority Patent Application JP 2010-137099 filed in the Japan Patent Office on Jun. 16, 2010, the entire contents of which are hereby incorporated by reference.

BACKGROUND

The present application relates to a muscle-activity diagnosis apparatus, method, and program. In particular, the present application relates to a muscle-activity diagnosis apparatus, method, and program that is capable of efficiently obtaining a change in myoelectric potential without much trouble in daily life, and is capable of identifying activity states of human muscles that are changing every moment.

Changes in myoelectric potential that occur with motion of facial-expression muscles are originated by motion of many muscles at the same time. Accordingly, it has been necessary to attach sensors to various parts of a human body in order to identify facial expressions from myoelectric signals (for example, refer to Japanese Unexamined Patent Application Publication Nos. 2000-285221, 10-143309, and 63-172322).

Also, it becomes possible to obtain biological information, such as a myoelectric potential, etc., from an external auditory canal of an ear as a device for obtaining biological information by integrating an apparatus, such as an earphone, etc., (for example, refer to Japanese Unexamined Patent Application Publication No. 2008-67911).

Further, in order to grasp a change in myoelectric potential quantitatively, a technique for applying Fourier transformation on detected data has been proposed (for example, refer to Japanese Unexamined Patent Application Publication No. 01-86936).

Also, a technique has been proposed in which wavelet transformation is applied to myoelectric-potential digital data to obtain a change in frequency in time (dynamic spectrum), and occurrence time of the change in the broad spectrum is detected so that motion-start time is detected automatically (for example, refer to Japanese Patent No. 3983989).

SUMMARY

However, if sensors are attached to various parts of a person as described in Japanese Unexamined Patent Application Publication Nos. 2000-285221, 10-143309, and 63-172322, it brings uncomfortable feeling to that person in daily life. For example, in order to grasp motion of facial-expression muscles to estimate a facial expression, and to operate a device on the basis of the estimated expression, a lot of electrodes are necessary to be attached on the face of that person, which brings much trouble to the person in daily life.

Also, by the technique described in Japanese Unexamined Patent Application Publication No. 2008-67911, very large noise occurs in an actual living environment, and thus it has been difficult to obtain a biological signal.

Further, as shown in Japanese Unexamined Patent Application Publication No. 01-86936, when a myoelectric activity of each part is detected by performing Fourier transformation, it is difficult to expect reliable detection result except that the signal waveforms have been stored for a considerable long period of time and then analyzed. Also, as shown in Japanese Patent No. 3983989, although it is possible to obtain activity-start time of a myoelectric potential by performing wavelet transformation, it has been difficult to identify a muscle that is acting.

The present application has been made in view of these circumstances. It is desirable to efficiently obtain a change in myoelectric potential without much trouble in daily life, and to identify activity states of human muscles that are changing every moment.

According to an embodiment, there is provided a muscle-activity diagnosis apparatus including: an acquiring section acquiring a myoelectric signal from a test subject; using the myoelectric signal as an original signal, a transformed-signal generating section generating a transformed signal by performing Hilbert transformation and inverse Fourier transformation on the original signal; a phase-velocity calculating section calculating a phase velocity of the myoelectric signal on the basis of phases of the original signal and the transformed signal; and on the basis of a plurality of feature quantities of a waveform of the myoelectric signal in a unit time and the plurality of feature quantities including at least a size of amplitude of the myoelectric signal and the calculated phase velocity, a state-identifying section identifying an activity state of a muscle of a predetermined part of a body of the test subject for each of the unit time.

In the above-described embodiment, the acquiring section differentially may detect an electronic signal obtained from an earphone sensor inserted into an external auditory canal of the test subject, and may digitize the signal so as to obtain the myoelectric signal.

In the above-described embodiment, the state-identifying section may identify activity states of muscles of a plurality of parts of a face of the test subject, and may output a signal indicating a facial expression of the test subject estimated on the basis of the identified activity states of the muscles of the plurality of parts.

In the above-described embodiment, the earphone sensor may be provided with a myoelectric electrode for detecting a electronic signal generated by muscle activity of the test subject; a voltage detection electrode for detecting a reference voltage being a difference between a potential in an ear of the test subject and a potential of a circuit in the earphone sensor; and a feedback electrode for supplying a feedback voltage generated by inversely amplifying the reference voltage.

In the above-described embodiment, using the plurality of feature quantities of the waveform of the myoelectric signal in the unit time provided in advance as parameters, the state-identifying section may perform machine learning on the basis of a sample having a corresponding relationship between the parameter and the activity state of the muscle of the test subject, and may identify the plurality of feature quantities of the myoelectric signal on the basis of a result of the machine learning so as to identify the activity state of the muscle of the predetermined part of the body of the test subject.

In the above-described embodiment, AdaBoost may be used as the identification method by the machine learning.

According to another embodiment, there is provided a method of diagnosing muscle activity, including: an acquiring section acquiring a myoelectric signal from a test subject; using the myoelectric signal as an original signal, a transformed-signal generating section generating a transformed signal by performing Hilbert transformation and inverse Fourier transformation on the original signal; a phase-velocity calculating section calculating a phase velocity of the myoelectric signal on the basis of phases of the original signal and the transformed signal; and on the basis of a plurality of feature quantities of a waveform of the myoelectric signal in a unit time and the plurality of feature quantities including at least a size of amplitude of the myoelectric signal and the calculated phase velocity, a state-identifying section identifying an activity state of a muscle of a predetermined part of a body of the test subject for each of the unit time.

According to another embodiment, there is provided a program for causing a computer to function as a muscle-activity diagnosis apparatus, the apparatus including: an acquiring section acquiring a myoelectric signal from a test subject; using the myoelectric signal as an original signal, a transformed-signal generating section generating a transformed signal by performing Hilbert transformation and inverse Fourier transformation on the original signal; a phase-velocity calculating section calculating a phase velocity of the myoelectric signal on the basis of phases of the original signal and the transformed signal; and on the basis of a plurality of feature quantities of a waveform of the myoelectric signal in a unit time and the plurality of feature quantities including at least a size of amplitude of the myoelectric signal and the calculated phase velocity, a state-identifying section identifying an activity state of a muscle of a predetermined part of a body of the test subject for each of the unit time.

By an embodiment, a myoelectric signal is acquired from a test subject; using the myoelectric signal as an original signal, a transformed signal is generated by performing Hilbert transformation and inverse Fourier transformation on the original signal; a phase velocity of the myoelectric signal is calculated on the basis of phases of the original signal and the transformed signal; and on the basis of a plurality of feature quantities of a waveform of the myoelectric signal in a unit time and the plurality of feature quantities including at least a size of amplitude of the myoelectric signal and the calculated phase velocity, an activity state of a muscle of a predetermined part of a body of the test subject is identified for each of the unit time.

By the present application, it is possible to efficiently obtain a change in myoelectric potential without much trouble in daily life, and to identify activity states of human muscles that are changing every moment.

Additional features and advantages are described herein, and will be apparent from the following Detailed Description and the figures.

BRIEF DESCRIPTION OF THE FIGURES

FIG. 1 is a block diagram illustrating an example of a configuration of a facial-expression detection apparatus according to an embodiment;

DETAILED DESCRIPTION

Figure 2A:
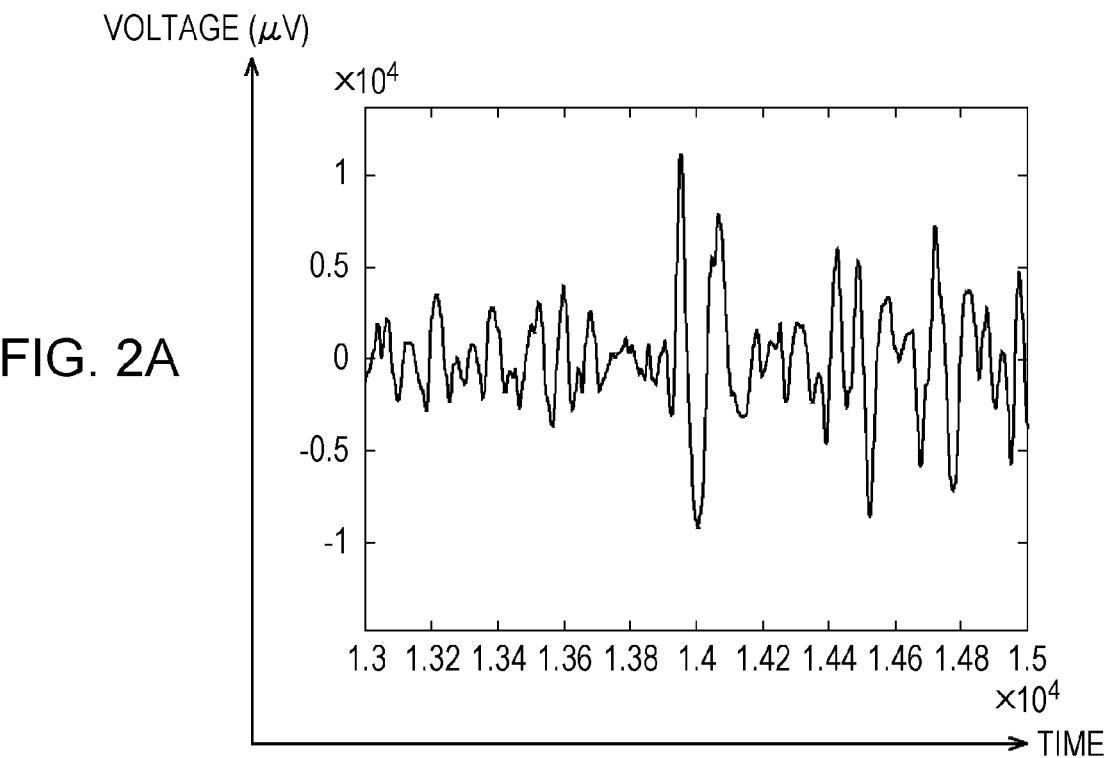
FIGS. 2A and 2B are diagrams illustrating waveforms of an original signal and a transformed signal, respectively.

Embodiments of the present application will be described below in detail with reference to the drawings.

FIG. 1 is a block diagram illustrating an example of a configuration of a facial-expression detection apparatus according to an embodiment.

The facial-expression detection apparatus 10 shown in the figure detects a myoelectric signal by an earphone sensor attached to an ear of a user 20, and identifies activities of facial muscles of the user 20 on the basis of the detected myoelectric signal. Thereby, it is possible to detect facial motion and expression of the user 20. In this regard, the myoelectric signal is a weak electronic signal that occurs when a muscle is activated.

It is noted that myoelectric signal shows a different frequency characteristic depending on a part of muscles that is acting. For example, it is noted that when cheek muscles are acting, a myoelectric signal having a relatively low-frequency signal component is output. Whereas it is noted that when jaw muscles are acting, a myoelectric signal having a relatively high-frequency signal component is output.

The facial-expression detection apparatus 10 analyzes a frequency characteristic of a myoelectric signal, and roughly identifies which part of the muscles are acting on the basis of the obtained frequency characteristic. Also, the facial-expression detection apparatus 10 identifies amounts of activities of the muscles of that part on the basis of amplitude of the myoelectric signal. And the facial-expression detection apparatus 10 detects motion and expression of the face of the user 20 on the basis of the parts of the muscles that are acting and the amount of the activities.

A detailed description will be given of the earphone sensor later. The earphone sensor is provided with myoelectric electrodes for detecting myoelectric signals, and a voltage detection electrode for adjusting a potential in the ear of the user 20 and a potential of a circuit in the earphone sensor, and a feedback electrode. The myoelectric electrode is connected to a signal line 51 and a signal line 52, and the voltage detection electrode and the feedback electrode are connected to a signal line 53 and a signal line 54, respectively.

The inverting amplifier filter circuit 48 inversely amplifies the reference voltage (the difference between a potential in the ear of the user 20 and a potential of a circuit in the earphone sensor) detected through the signal line 53 so as to generate a feedback voltage, and supplies the voltage to the signal line 54.

In this regard, the facial-expression detection apparatus 10 may be configured not to have the inverting amplifier filter circuit 48.

The myoelectric signal detected by the earphone sensor is input into the input-signal processing section 41 through the signal line 51 and the signal line 52. The input-signal processing section 41 amplifies the difference between the electronic signals obtained from the signal line 51 and the signal line 52, respectively, and outputs the signal.

The input-signal processing section 41 includes, for example, a differential detection section, a filter, and an amplifier in the inside. In the differential detection section, the signals obtained from the signal line 51 and the signal line 52 are coupled by a capacitor of about 0.1 μF, and are put through an instrumentation amplifier having an input impedance of 10 GΩ or more to generate a differential signal.

The filter includes, for example, a band-pass filter and a notch filter so that noise of the differential signal is eliminated. It is desirable that the filter has, for example, the second order or more of band-pass filters that pass from 100 Hz to 1 kHz (desirably the fourth), and the filter has a Q factor from 0.3 to 0.8. And since a signal of 50 Hz is very large, notch filters of the fourth order are inserted.

The signal output from the filter is amplified by an amplifier, and is output. The amplifier having a variable amplification factor of between 1,000 to 50,000 inclusive is used.

In this regard, the configuration of the above-described input-signal processing section 41 is an example, and a configuration different from this may be employed.

The signal output from the input-signal processing section 41 is supplied to an AD converter 42, and is converted into digital data. The AD converter 42 samples the signal, for example, at a sampling rate of between 1,000 samples/sec and 40,000 samples/sec inclusive, and supplies the signal to a Hilbert transformation section 43, a phase-diagram generation section 45, and a state detection section 47.

In this regard, the signal output from the AD converter 42 is a signal produced by eliminating noise from the myoelectric signal actually detected from the earphone sensor, is amplified, and then is sampled to be subjected to waveform shaping. Thus, this signal ought to be regarded as the myoelectric signal.

The Hilbert transformation section 43 performs Hilbert transformation on the signal output from the AD converter 42.

Here, a description will be given of the Hilbert transformation.

An operator of the Fourier transformation is denoted by X. The Fourier transformation on a predetermined frequency ω is expressed by Expression (1). In this regard, e in the expression denotes a base in natural logarithm.

$$X(e^{i\omega}) = X_r(e^{i\omega}) + iX_i(e^{i\omega}) \; (X_r(e^{i\omega}) \text{ the real part}, X_i(e^{i\omega}) \text{ the imaginary part)} \quad (1)$$

Now, Expression (2), in which the real part of Expression (1) is expressed by the imaginary part, is defined as follows.

$$X_r(e^{i\omega}) = \frac{1}{H(e^{i\omega})} X_i(e^{i\omega}) = -H(e^{i\omega}) X_i(e^{i\omega}) \quad (2)$$

The operation denoted by an operator H shown in Expression (2) is Hilbert transformation. In the Hilbert transformation, in the same manner as Fourier transformation, a predetermined value is calculated as an element for each of a plurality of frequencies ω. Now, assuming that there are n frequencies ω, an element h [n] that is calculated for the n-th frequency $\omega_n$ by the Hilbert transformation is expressed by Expression (3).

$$h[n] = \frac{1}{2\pi} \int_{-\pi}^{0} i e^{i\omega n} d\omega = \frac{1}{2\pi} \int_{0}^{\pi} i e^{i\omega n} d\omega \quad (3)$$

The Hilbert transformation section 43 individually outputs n elements expressed by Expression (3), which are produced by performing Hilbert transformation on the signal (called the original signal) output from the AD converter 42.

The inverse-Fourier-transformation section 44 performs inverse Fourier transformation on the n elements output from the Hilbert transformation section 43. Thereby, in the entire frequency band, signals having waveforms with a phase shifted 90° with respect to the phase of the original signal are generated.

The phase-diagram generation section 45 generates a phase diagram on the basis of the original signal and the signal (called the transformed signal) output from the inverse-Fourier-transformation section 44. The phase-diagram generation section 45 generates a phase diagram in which a value of the original signal is plotted on the horizontal axis, and a value of the transformed signal is plotted on the vertical axis.

Figure 2B:
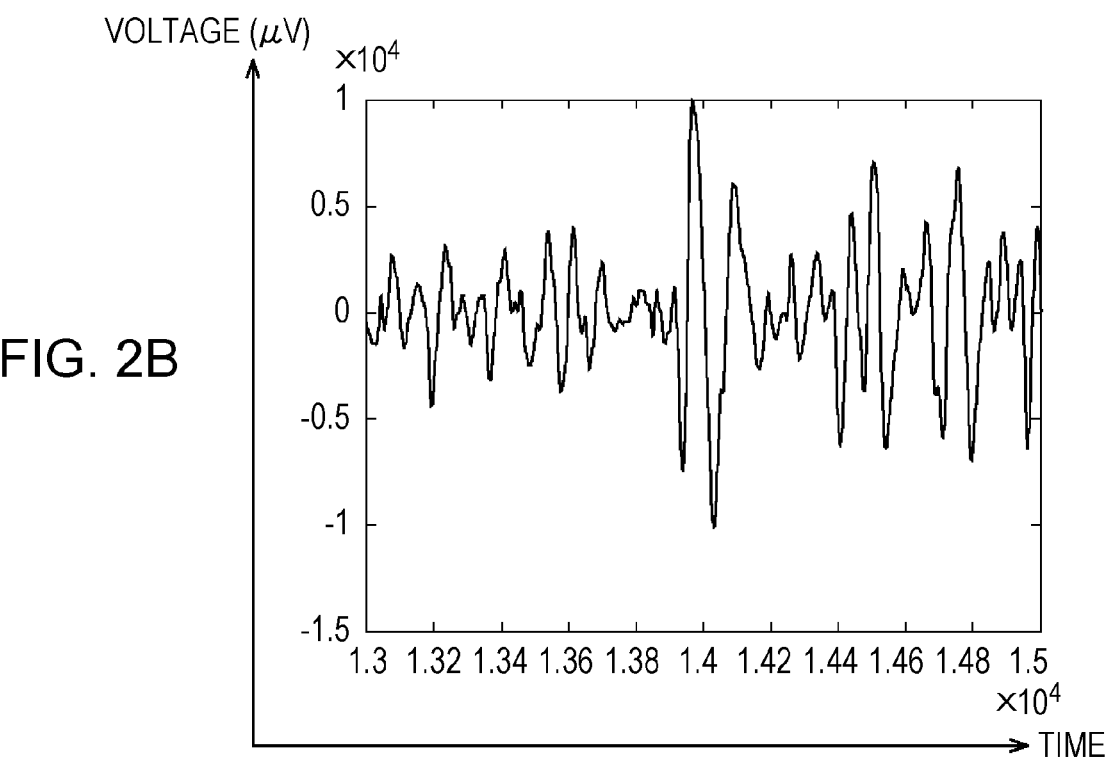

FIGS. 2A and 2B are diagrams illustrating waveforms of an original signal and a transformed signal, respectively. In FIG. 2A, the horizontal axis shows time, the vertical axis shows voltage, and the waveform of the original signal is shown. In FIG. 2B, the horizontal axis shows time, the vertical axis shows voltage, and the waveform of the transformed signal is shown. The phase of the waveform in FIG. 2B is shifted 90° with respect to the phase of the waveform in FIG. 2A at the same time.

Figure 3:
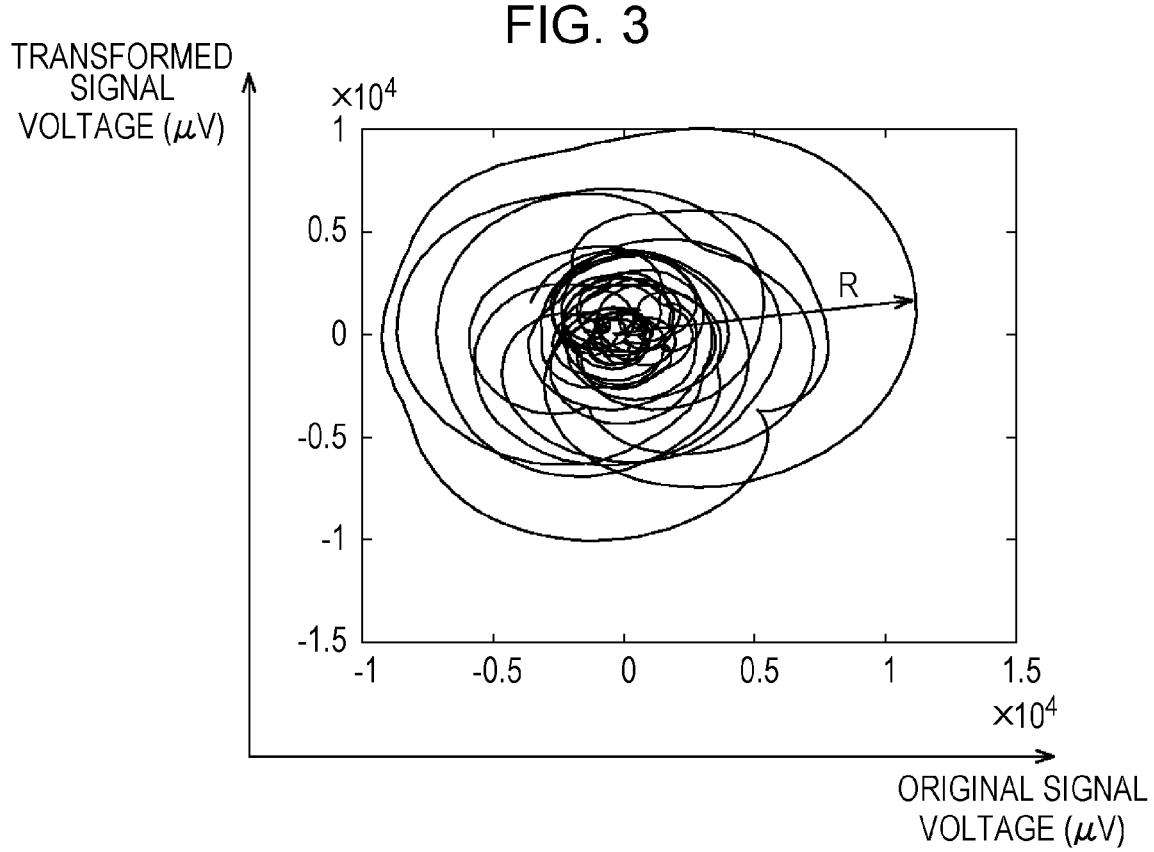
FIG. 3 is a diagram illustrating an example of a phase diagram.

FIG. 3 is a diagram illustrating an example of a phase diagram which is generated on the basis of the original signal shown in FIG. 2A and the transformed signal shown in FIG. 2B. In FIG. 3, the horizontal axis shows voltage of the original signal, and the vertical axis shows voltage of the transformed signal. In FIG. 3, a waveform is shown by plotting voltage of the original signal and voltage of the transformed signal at the same time in the same manner as drawing loops. In the figure, with the coordinates (0, 0) as center of the waveform (loop), a distance denoted by a line R represents amplitude of the original signal (or the transformed signal).

In this regard, the phase-diagram generation section 45 does not generate and display the phase diagram as shown in FIG. 3, etc., but actually generates data corresponding to the phase diagram. That is to say, the phase diagram shown in FIG. 3 is created virtually as it were.

Figure 4:
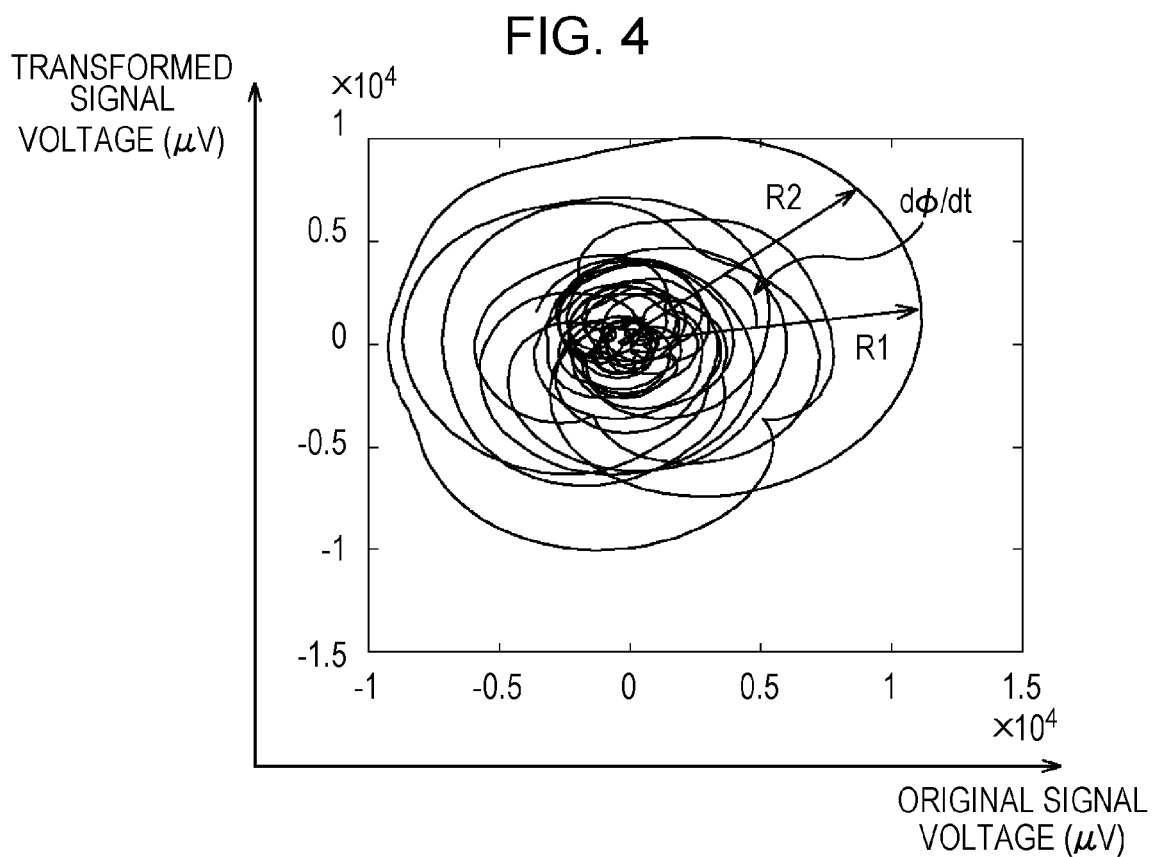
FIG. 4 is an explanatory diagram of a phase velocity.

Referring back to FIG. 1, the phase-velocity calculation section 46 calculates a phase velocity of the signal on the basis of the phase diagram generated by the phase-diagram generation section 45. The phase velocity is obtained, for example, as shown in FIG. 4, by identifying a line R1 and a line R2 in the figure, which are two amplitudes in a waveform like drawing loops, and dividing an angle φ therebetween by the time period.

Figure 5:
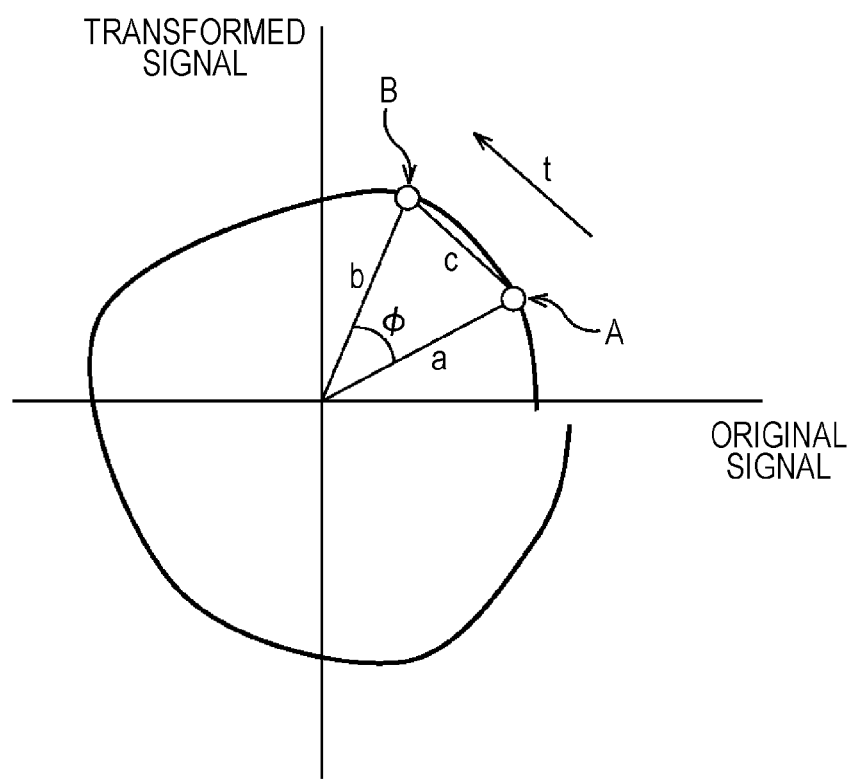
FIG. 5 is an explanatory diagram of a method of calculating a phase velocity.

Using the phase diagram generated by the phase-diagram generation section 45, the phase-velocity calculation section 46 obtains, for example, coordinates of a position A and coordinates of a position B, as shown in FIG. 5, which are coordinates changing with time t. And the phase-velocity calculation section 46 calculates the phase (angle) φ as follows. That is to say, a triangle is formed by the point A, the point B, and the center point in FIG. 5. When lengths of individual sides of the triangle are denoted by a, b, and c, the phase φ can be calculated by Expression (4) and Expression (5).

$$\cos\phi = \frac{b^2 + c^2 - a^2}{2bc} \quad (4)$$

$$\phi = \sin^{-1}(1 - \cos^2\phi) \quad (5)$$

As shown by Expression (5), it is possible to keep the calculation sensitivity high by obtaining arcsine of φ even if it is a short time and φ has a small value. Here, the phase velocity can be obtained by dividing the calculated φ by time t. The phase-velocity calculation section 46 calculates φ in this manner.

Here, the phase velocity is calculated. However, if the phase velocity is identified, the frequency of the myoelectric signal can also be identified. As described above, a myoelectric signal represents a different frequency characteristic depending on a part of the muscle that is acting. That is to say, in place of detecting the frequency of the myoelectric signal, the phase velocity is calculated. For example, when detecting a frequency of a signal, it is necessary to wait for the signal to oscillate at least one cycle. However, the phase velocity can be calculated without waiting for the signal to oscillate one cycle.

Figure 6:
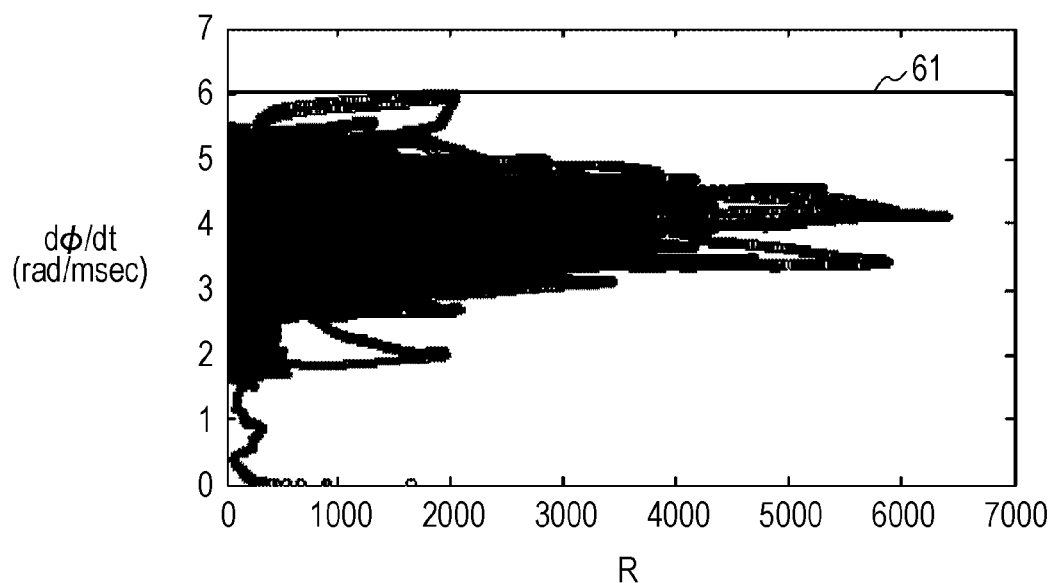
FIG. 6 is a diagram illustrating a phase velocity of a myoelectric signal when a human cheek muscle is acting.
Figure 7:
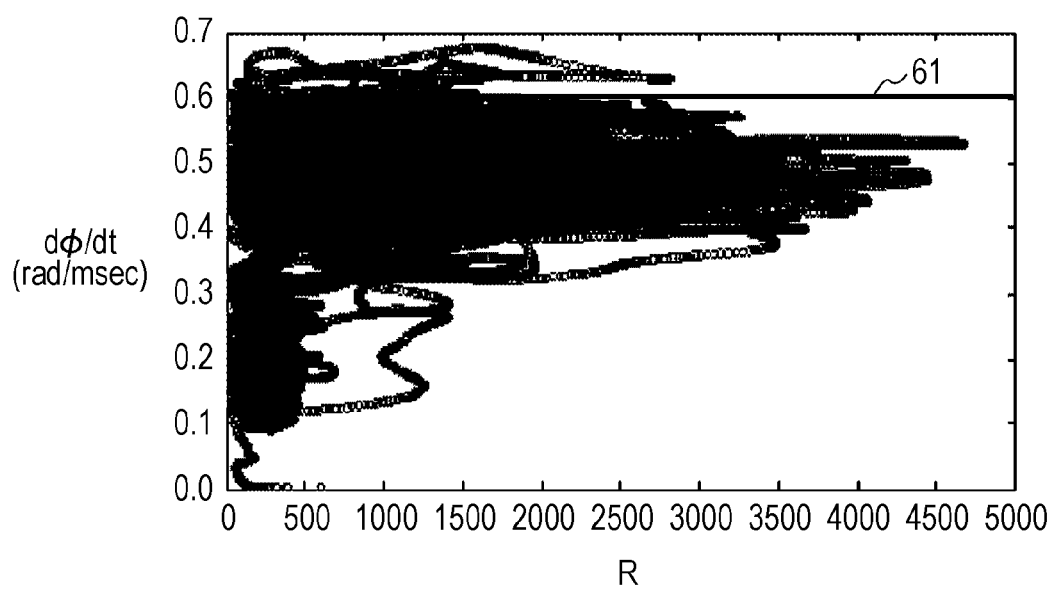
FIG. 7 is a diagram illustrating a phase velocity of a myoelectric signal when a human jaw muscle is acting.

FIG. 6 is a diagram illustrating a phase velocity of a myoelectric signal when a human cheek muscle is acting. FIG. 7 is a diagram illustrating a phase velocity of a myoelectric signal when a human jaw muscle is acting. In FIG. 6 and FIG. 7, the horizontal axis shows amplitude of the myoelectric signal (the line R shown in FIG. 3), the vertical axis shows phase velocity of the myoelectric signal, and a change in the phase velocity of the myoelectric signal is shown as a waveform.

As shown in FIG. 6, when cheek muscles are acting, the phase velocity does not exceed the threshold value shown by a line 61 regardless of the amplitude of the electric signal. On the other hand, as shown in FIG. 7, when jaw muscles are acting, the phase velocity of the myoelectric signal exceeds the threshold value shown by the line 61.

In this manner, for example, by comparing the phase velocity with the threshold value, it is possible to estimate whether jaw muscles are mainly acting now, or cheek muscles are mainly acting.

Referring back to FIG. 1, as described above, the phase-velocity calculation section 46 outputs the calculated myoelectric-signal phase velocity in association with time. That is to say, the phase velocity of the signal output from the AD converter 42 at each time is calculated by the phase-velocity calculation section 46, and the phase velocity information at each time is output to the state detection section 47. In this regard, the information is output, for example, as a signal indicating a change in the phase velocity with passage of time.

The state detection section 47 outputs a signal identifying facial motion and expression, etc., of the user 20 on the basis of the signal output from the AD converter 42 and the signal output from the phase-velocity calculation section 46.

Figure 8:
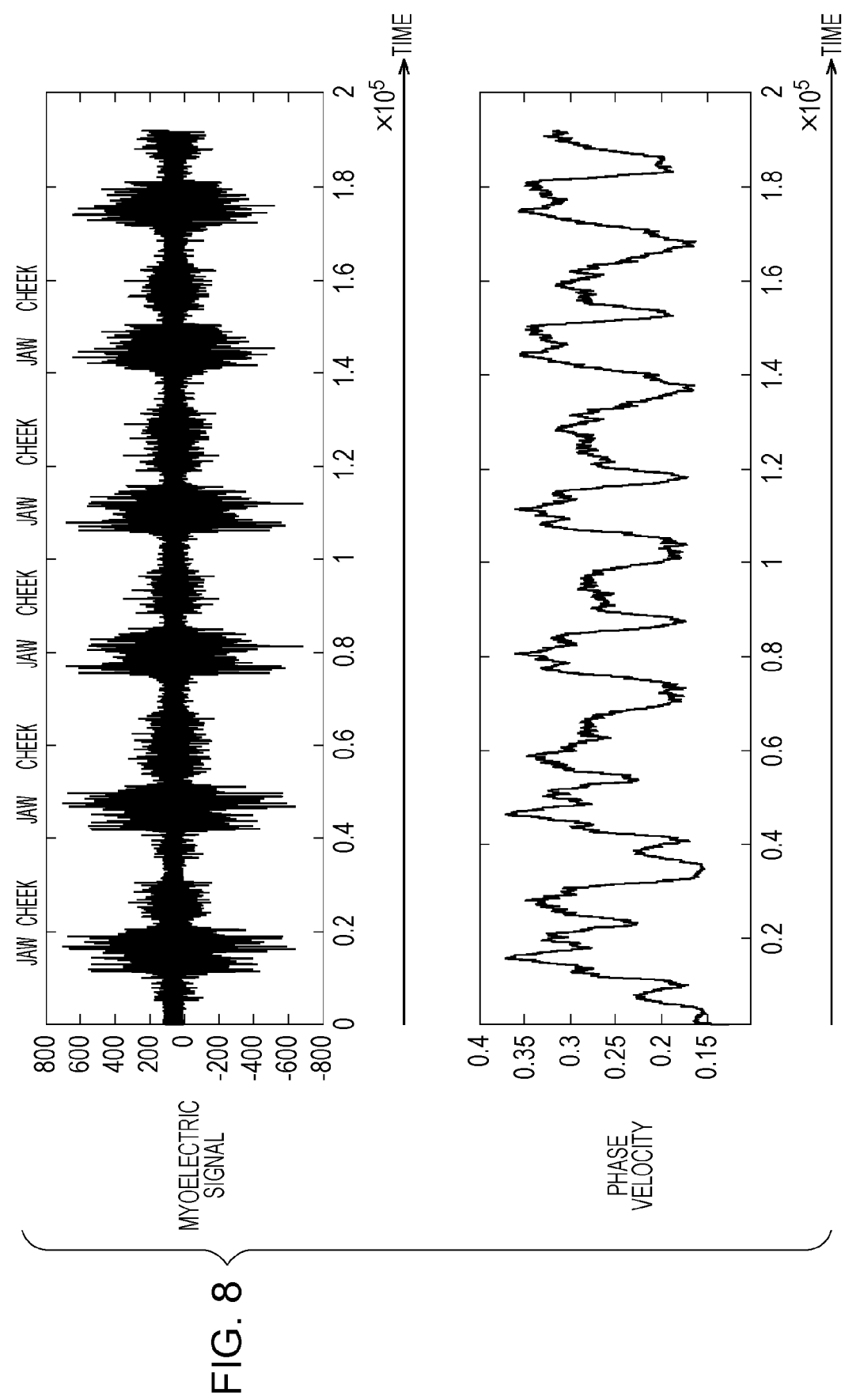
FIG. 8 is an explanatory diagram of an example in which facial motion and expression are identified on the basis of a phase velocity of a myoelectric signal and amplitude of the myoelectric signal.

FIG. 8 is an explanatory diagram of an example in which facial motion and expression of the user 20 are identified on the basis of the phase velocity of the myoelectric signal and the amplitude of the myoelectric signal. In FIG. 8, a graph in the upper part of the figure shows a waveform of the myoelectric signal (the signal output from the AD converter 42) with time as the horizontal axis and voltage value as the vertical axis. In FIG. 8, a graph in the lower part of the figure shows a change in the phase velocity (the waveform of the signal output from the phase-velocity calculation section 46) of the myoelectric signal shown in the upper part of the figure with time as the horizontal axis, and phase velocity value as the vertical axis.

On the basis of the waveform of the graph in the upper part of the figure, for example, it is possible to estimate which part of the face muscles of the user 20 is acting by threshold-value determining the size of the amplitude, etc. To put it in another way, if the amplitude size of the waveform of the graph in the upper part of the figure is less than a threshold value, it is thought that the face muscles of the user 20 are scarcely acting.

Also, for example, as described with reference to FIG. 6 and FIG. 7, it is possible to set a threshold value of the phase velocity for determining part of the muscles that is acting, and to estimate which muscle in the face muscles of the user 20 is acting on the basis of the waveform of the graph in the lower part of FIG. 8.

In this manner, as shown above the upper graph of FIG. 8, the state detection section 47 identifies which muscle among the face muscles of the user 20 is acting at each time (actually, for each unit time) as "jaw", "cheek", . . . .

In this regard, here, a description has been given of the example in which a threshold-value determination is made on the size of the amplitude and the phase velocity. As described later, a plurality of samples may be subjected to machine learning, and which part of the face muscles of the user 20 is mainly acting may be identified.

If the state detection section 47 identifies that, for example, a cheek muscle is mainly acting, it is thought that the user 20 is smiling, and thus the state detection section 47 outputs a signal corresponding to a facial expression "smile". Also, for example, if the state detection section 47 identifies that a jaw muscle is acting, it is thought that the user 20 has an uncomfortable facial expression. Accordingly, the state detection section 47 output a signal corresponding to an expression "uncomfortable". Alternatively, signals related to a part of muscles, such as a "cheek", a "jaw", etc., may be output.

The state detection section 47 outputs the signal identifying the facial motion and expression, etc., of the user 20 in this manner.

If the signal output from the state detection section 47 is transmitted to another device, for example, it becomes possible for the user 20 to operate the device only by changing the facial expression.

As described above, in the present application, the myoelectric signal is subjected to Hilbert transformation, and is subjected to inverse Fourier transformation to calculate the phase velocity from the phase diagram based on the original signal and the transformed signal.

For example, to date, a muscle activity of each part has been detected by performing Fourier transformation on a myoelectric signal and analyzing a frequency characteristic.

Figure 9:
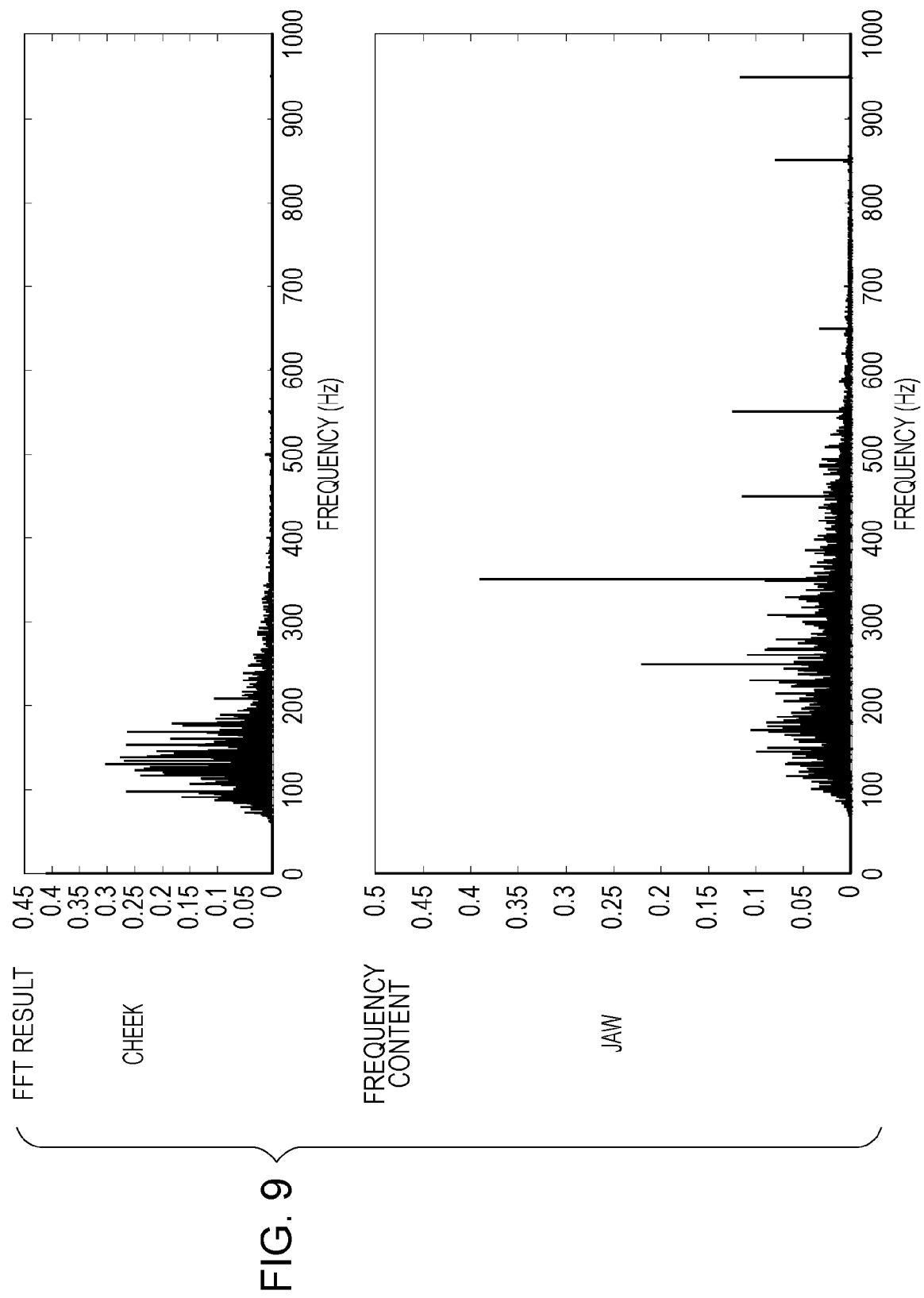
FIG. 9 is a diagram illustrating an example of a frequency spectrum of a myoelectric signal.

FIG. 9 is a diagram illustrating an example of a frequency spectrum of a myoelectric signal when a human cheek muscle is moved and when a human jaw muscle is moved. In FIG. 9, the horizontal axis shows frequency, and the vertical axis shows power. The upper part of FIG. 9 illustrates a frequency spectrum when the cheek muscle is moved. The lower part of FIG. 9 illustrates a frequency spectrum when the jaw muscle is moved.

As shown in FIG. 9, it is understood that when a cheek muscle is acting, the myoelectric signal having a relatively large low-frequency signal component is output, and when a jaw muscle is acting, the myoelectric signal having a relatively large high-frequency signal component is output. In this manner, if the myoelectric signal is subjected to Fourier transformation in order to obtain a frequency spectrum, it is possible to identify which part of the muscles is mainly acting.

However, when a frequency spectrum is obtained by performing Fourier transformation on the myoelectric signal, it is difficult to expect reliable detection result except that the signal waveforms have been stored for a considerable long period of time and then analyzed. For example, in order to obtain the frequency spectrum shown in FIG. 9, it takes 10 seconds or more.

It is thought that human facial motion and expression does not normally continue without change for a long time, but changes every moment. Accordingly, by a method of performing Fourier transformation on the myoelectric signal to obtain a frequency spectrum, it is difficult to precisely identify human facial motion and expression in sequence.

In contrast, in the present application, the myoelectric signal is subjected to Hilbert transformation, and then is subjected to inverse Fourier transformation to obtain the phase velocity using the phases of the original signal and the transformed signal. Thus, it is possible to identify which part of the muscles is mainly acting. Accordingly, in comparison with related-art techniques, it becomes possible to make the storage time of the signal waveform very short (for example, about 0.4 second).

That is to say, in the present application, for example, the waveform of the myoelectric signal is analyzed for each unit time of about 0.4 second, and the phase velocity and the size of the amplitude are obtained. Thereby, it is possible to detect the facial motion and expression of the user 20 in each unit time. In this manner, it becomes possible to precisely identify human facial motion and expression in sequence.

In this manner, the facial-expression detection apparatus 10 detects the facial motion and expression of the user 20.

Next, a description will be given of an earphone sensor.

Figure 10:
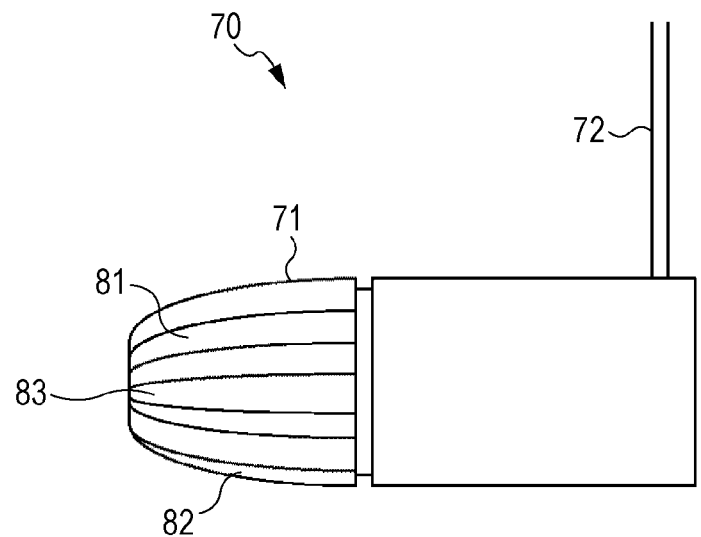
FIG. 10 is a side view of an earphone sensor.

FIG. 10 is a side view of an earphone sensor 70. As shown in FIG. 10, the earphone sensor 70 is provided with an earpiece 71 formed by a soft material, such as low-resilience polyurethane, silicone resin, polypropylene, soft rubber, etc., at an end. And electrodes are attached on the earpiece 71. In FIG. 10, a myoelectric electrode 81, a myoelectric electrode 82, and a voltage detection electrode 83 are attached. Also, as described later, a feedback electrode 84 is attached to a blind spot in FIG. 10.

In this regard, as described above, the voltage detection electrode 83 is an electrode for detecting a reference voltage that is a difference between a potential in an ear of the user 20 and a potential of a circuit in the earphone sensor. Also, the feedback electrode 84 is an electrode for supplying a feedback voltage occurred by inversely amplifying the reference voltage.

The various electrodes, which are made by attaching silver, silver chloride, etc., on a film-state material, such as a double-sided adhesive tape, a PET film, etc., are attached on the earpiece 71 in order to prevent wrinkles caused by bending. In this regard, in order to prevent the earpiece 71 from being stuck, etc., when inserted into an ear, the earpiece 71 ought to be provided with gutters in which various electrodes are embedded.

The signals detected by the various electrodes are transmitted through signal lines in a cable 72. In this regard, the cable 72 internally includes the signal line 51 to the signal line 54 described above with reference to FIG. 1.

Figure 11:
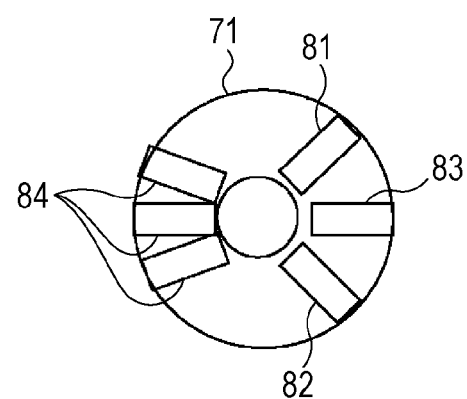
FIG. 11 is a front view of the earphone sensor of FIG. 10.

FIG. 11 is a front view, taken from the left side of FIG. 10, of the earpiece 71. As shown in FIG. 11, a feedback electrode 84 including three electrodes is attached to the left side in the figure of the earpiece 71. Also, a myoelectric electrode 81, a myoelectric electrode 82, and a voltage detection electrode 83 are attached to the right side in the figure. The voltage detection electrode 83 is attached so as to be disposed between the myoelectric electrode 81 and the myoelectric electrode 82.

Figure 12:
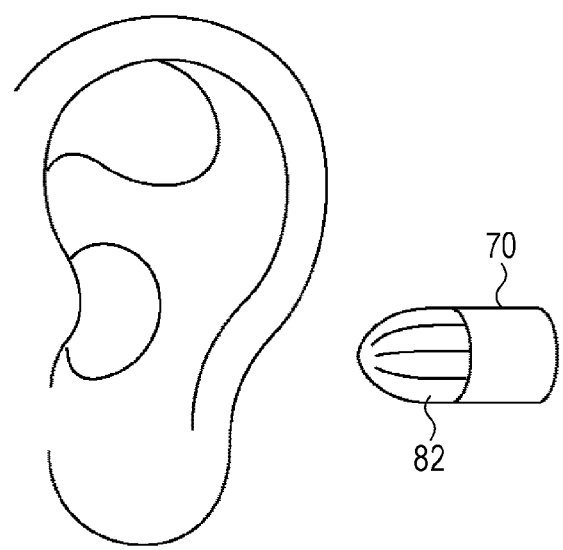
FIG. 12 is an explanatory diagram of attaching the earphone sensor.

FIG. 12 is an explanatory diagram of attaching the earphone sensor 70. When the earphone sensor 70 is attached to an ear of the user 20, as shown in the figure, the earphone sensor 70 is inserted into the external auditory canal with the myoelectric electrode faced toward a tragus.

In this regard, in order not to make a mistake in the insertion direction of the earphone sensor 70, for example, the earpiece 71 may have a special shape. That is to say, when the user 20 inserts the earphone sensor 70 into the external auditory canal, it is desirable that the earpiece 71 has a shape so that the user 20 is forced to direct the myoelectric electrode toward a tragus.

In this manner, by the present application, it is possible to identify the facial expression and motion of the face of the user 20 only by inserting the earphone sensor 70 into an ear of the user 20.

For example, if the motion of facial-expression muscles is learned, the facial expression is estimated, and devices are to be operated on the basis of the estimated facial expression using related-art techniques, many electrodes are necessary to be attached to the face. This brings much trouble to the user in daily life.

On the other hand, in the present application, it is only necessary to insert the earphone sensor 70 into an ear, and thus it does not bring much trouble to the user in daily life.

Next, a description will be given of machine learning. As described above, the state detection section 47 of the facial-expression detection apparatus 10 may identify the facial expression and the facial motion of the user 20 on the basis of a machine learning result.

Here, it is assumed that "AdaBoost" is used as a method of machine learning. "AdaBoost" is a method of repeatedly conducting learning in a boundary area at the time of learning, and enabling effective separation (identification) on the case that results in a failure by one-time learning. The above-described combination of the amplitude size of the myoelectric signal and the phase velocity are used as machine learning parameters.

Figure 13:
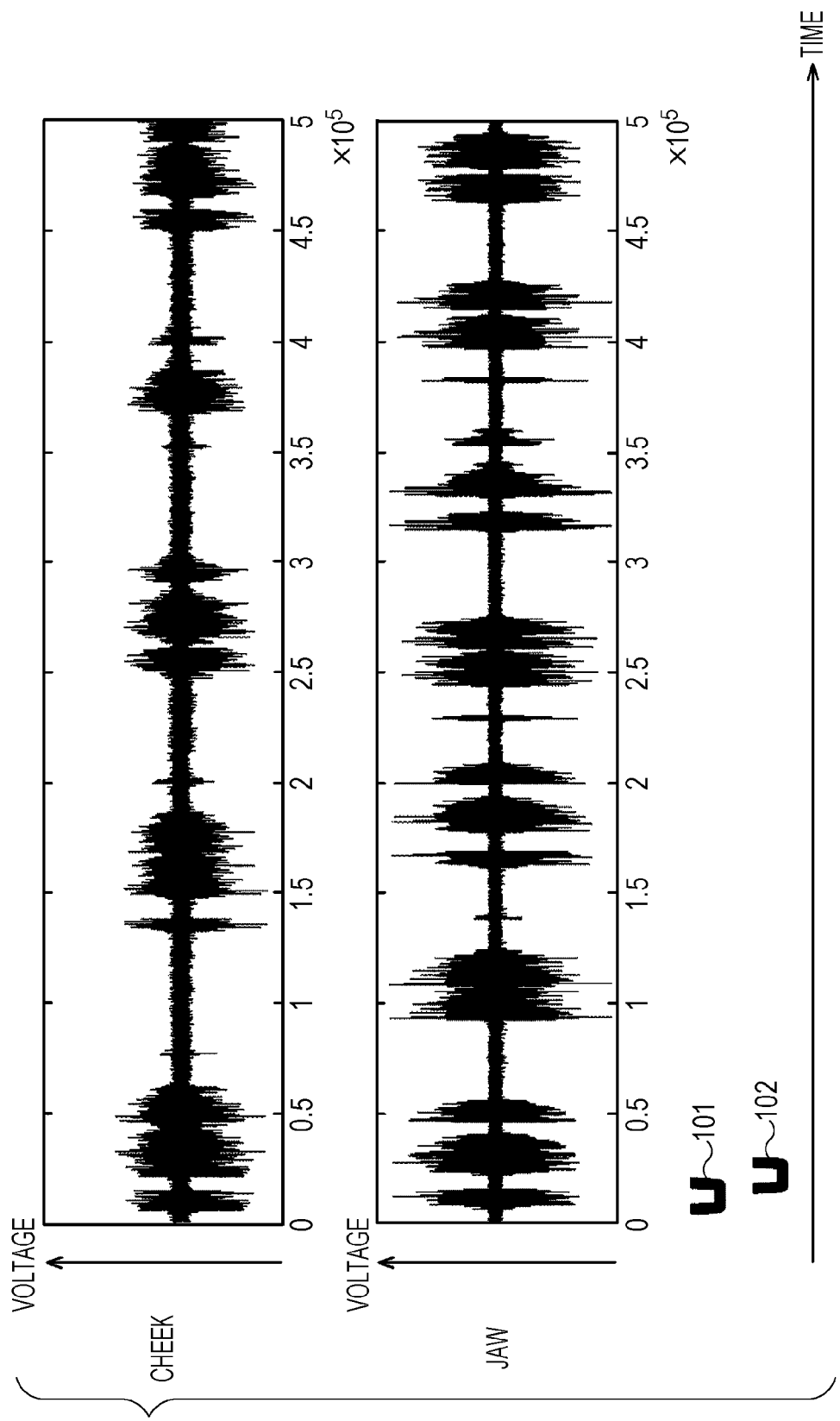
FIG. 13 is an explanatory diagram of a machine learning of a myoelectric signal.

For example, the myoelectric signal as shown in FIG. 13 is divided into 0.4-second frames, and 50 samples are provided for three states ("rest (without expression)", "smile", and "chew") of the face of the user 20. In FIG. 13, the horizontal axis shows time, the vertical axis shows voltage, and the waveform of the myoelectric signal (the signal output from the AD converter 42) is shown.

The waveform of the upper graph in FIG. 13 is a waveform of the myoelectric signal when the cheek muscle is acting. In this case, the face state of the user 20 becomes "smile". The waveform of the lower graph in FIG. 13 is a waveform of the myoelectric signal when the jaw muscle is acting. In this case, the face state of the user 20 becomes "chew". In this regard, although not shown in the figure, the myoelectric signal when the face state of the user 20 is "rest" is also obtained and learned.

U-shaped graphic symbols 101 and 102, shown at the bottom of FIG. 13 represent a time period of 0.4-second frame. The waveform of the myoelectric signal is divided by such a frame.

When machine learning is conducted, 50 0.4-second frames are created for each myoelectric signal in the three states, "rest", "smile", and "chew", and the waveform of each frame is obtained. And, the combinations of amplitude sizes of the waveform and the phase velocity are learned as learning parameters in association of "rest", "smile", or "chew" individually. Further, on the basis of the learning result, the face state of the user 20 is identified from the actually input myoelectric signal.

Figure 14:
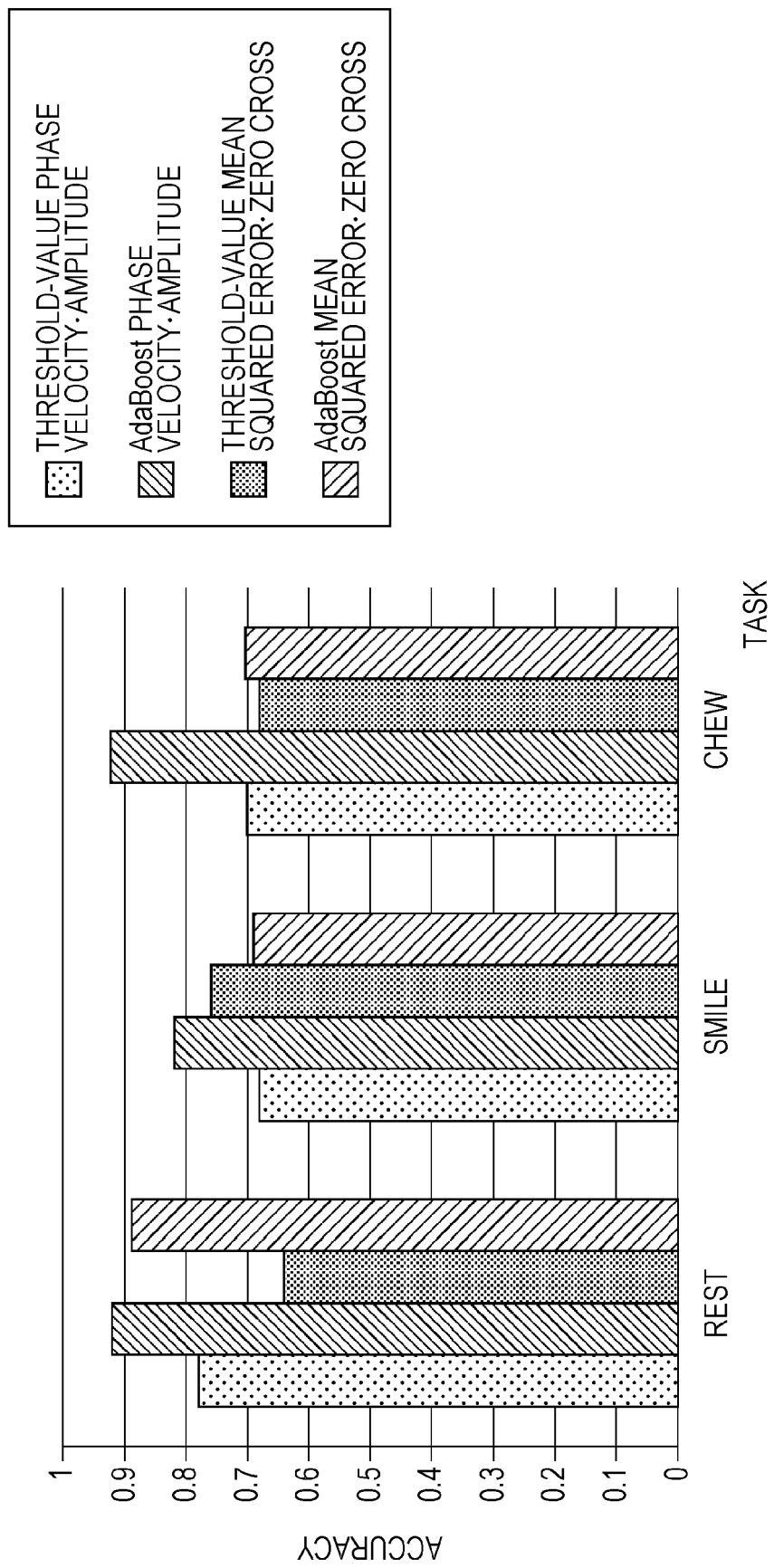
FIG. 14 is an explanatory diagram of advantages of the machine learning.

FIG. 14 is an explanatory diagram of advantages of the machine learning. In FIG. 14, comparisons are made between a method of identification by machine learning and a method of identification not by machine learning for the three states, "rest", "smile", and "chew", and the precision of the identification is calculated using "10-fold cross-validation". In this regard, "10-fold cross-validation", 90% of all the data is used as learning data, and the rest 10% is used as test data in order to identify the face state of the user 20.

Here, as described above, "AdaBoost" is employed as a method of identification by machine learning, and simple threshold-value determination is employed as a method of identification not by machine learning. Also, here, for the comparison of learning parameters, in addition to the combination of the size of amplitude and the phase velocity, the combination of a number zero crosses and a mean squared error is also employed. In this regard, here, the size of amplitude, the phase velocity, the number of zero crosses, the mean squared error are individually feature quantities extracted from the waveform of each frame.

In FIG. 14, cases having the description "threshold-value phase velocity·amplitude" represent right answer rates when the combination of the size of amplitude and the phase velocity is used for the parameters, and the face state of the user 20 is identified by a simple threshold-value determination.

Also, in FIG. 14, cases having the description "AdaBoost phase velocity·amplitude" represent right answer rates when the combination of the size of amplitude and the phase velocity is used for the parameters, and the face state of the user 20 is identified by "AdaBoost".

Further, in FIG. 14, cases having the description "threshold-value mean squared error·zero cross" represent right answer rates when the combination of the number of zero crosses and the mean squared error is used for the parameters, and the face state of the user 20 is identified by a simple threshold-value determination.

Also, in FIG. 14, cases having the description "AdaBoost mean squared error·zero cross" represent right answer rates when the combination of the number of zero crosses and the mean squared error, and the face state of the user 20 is identified by "AdaBoost".

As shown in FIG. 14, the cases where, in the individual three states "rest", "smile", and "chew", the combination of the size of amplitude and the phase velocity is used for the parameters, and identification is performed by the machine learning ("AdaBoost") have the highest right answer rates.

In this regard, as a method of identification by machine learning, "neural network", "linear determination", "support vector machine", etc., may be employed other than "AdaBoost". Also, for parameters, a larger number of feature quantities may be used. For example, the combination of the size of amplitude, the phase velocity, and feature quantities, such as a number of zero crosses, a mean squared error, a cepstrum coefficient, a frequency band power, etc., may be used for the parameters.

Also, the three states, "rest", "smile", and "chew", shown here are examples. It is also possible to identify the other states using parameters including the size of amplitude and the phase velocity.

Figure 15:
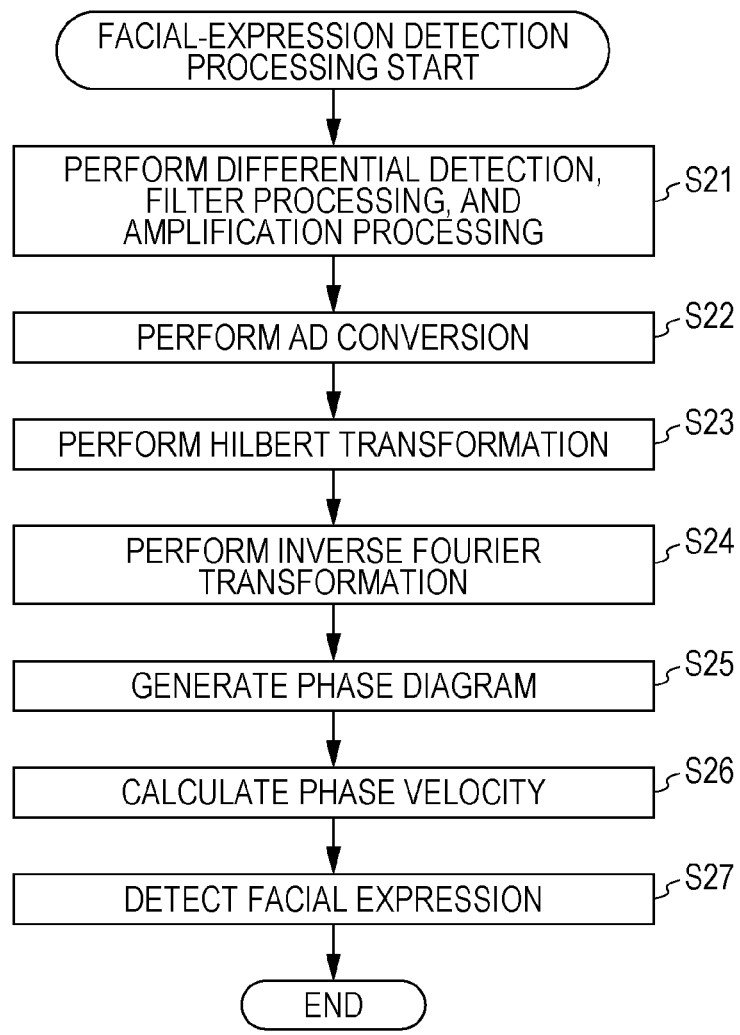
FIG. 15 is a flowchart illustrating an example of facial-expression detection processing.

Next, a description will be given of an example of facial-expression detection processing by the facial-expression detection apparatus 10 according to the present application with reference to a flowchart in FIG. 15.

In step S21, the input-signal processing section 41 performs differential detection on the myoelectric signals (the signals on the signal line 51 and the signal line 52) detected by the earphone sensor 70. And the input-signal processing section 41 performs filter processing by the band-pass filter and the notch filter to eliminate noise of the differentially-detected signal having been subjected to the filter processing, and amplifies the signal using the amplifier.

In step S22, the AD converter 42 performs AD conversion on the signal generated by the processing in step S21. At this time, for example, the signal generated by the processing in step S21 is sampled at a predetermined sampling rate to generate a signal.

In this regard, the signal generated in step S22 becomes the above-described original signal.

In step S23, the Hilbert transformation section 43 performs Hilbert transformation on the signal generated in step S22. At this time, for example, n elements calculated by the above-described Expression (3) are individually output.

In step S24, the inverse-Fourier transformation section 44 performs inverse Fourier transformation on the n elements that are output from the Hilbert transformation section 43 in step S23. Thereby, a signal having a waveform with a phase shifted 90° with respect to the phase of the original signal (the signal generated in step S22) is generated in the entire frequency band.

In this regard, the signal generated in step S24 becomes the above-described transformed signal.

In step S25, the phase-diagram generation section 45 generates a phase diagram on the basis of the original signal and the transformed signal (the signal generated in step S24). At this time, for example, the phase diagram (actually the data corresponding to the phase diagram) as described with reference to FIG. 3 is generated.

In step S26, the phase-velocity calculation section 46 calculates the phase velocity on the basis of the phase diagram generated in the processing in step S25. At this time, for example, the operations of Expression (4) and Expression (5) are performed as described above with reference to FIG. 4 and FIG. 5, and the phase velocity is calculated. And, the phase-velocity calculation section 46 outputs the calculated phase velocity in association with time. That is to say, the phase velocity at each time of the signal output from the AD converter 42 is calculated by the phase-velocity calculation section 46, and is output to the state detection section 47 as a signal indicating a change in the phase velocity with the passage of time.

In step S27, the state detection section 47 detects the facial expression of the user 20 (or the facial motion, etc.). At this time, the state detection section 47 outputs a signal identifying the facial motion and the facial expression of the user 20 on the basis of the signal generated by the processing in step S22 and the signal of the phase velocity obtained by the processing in step S26. For example, as shown by the upper graph in FIG. 8, the signal identifying which muscle among the facial muscles of the user 20 is mainly acting at each time as "jaw", "cheek", . . . , is output.

In this manner, the facial-expression detection processing is performed.

The description has been given of an example in which the facial motion and expression of the user 20 is detected by inserting the earphone sensor 70 into an ear of the user 20. However, if the sensor is attached to a hand or a foot of the user 20, it becomes possible to detect a state of the hand or the foot of the user 20 at each time. That is to say, the present application can be applied not only to a facial-expression detection apparatus, but also to a general muscle-activity diagnosis apparatus.

In this regard, the above-described series of processing can be executed by hardware or by software. When the series of processing is executed by software, programs constituting the software may be installed in a computer built in a dedicated hardware from a network or a recording medium. Alternatively, the various programs may be installed from a network or a program recording medium, for example, in a general-purpose personal computer 700 illustrated in FIG. 16, etc., which is capable of executing various functions by installing various programs.

Figure 16:
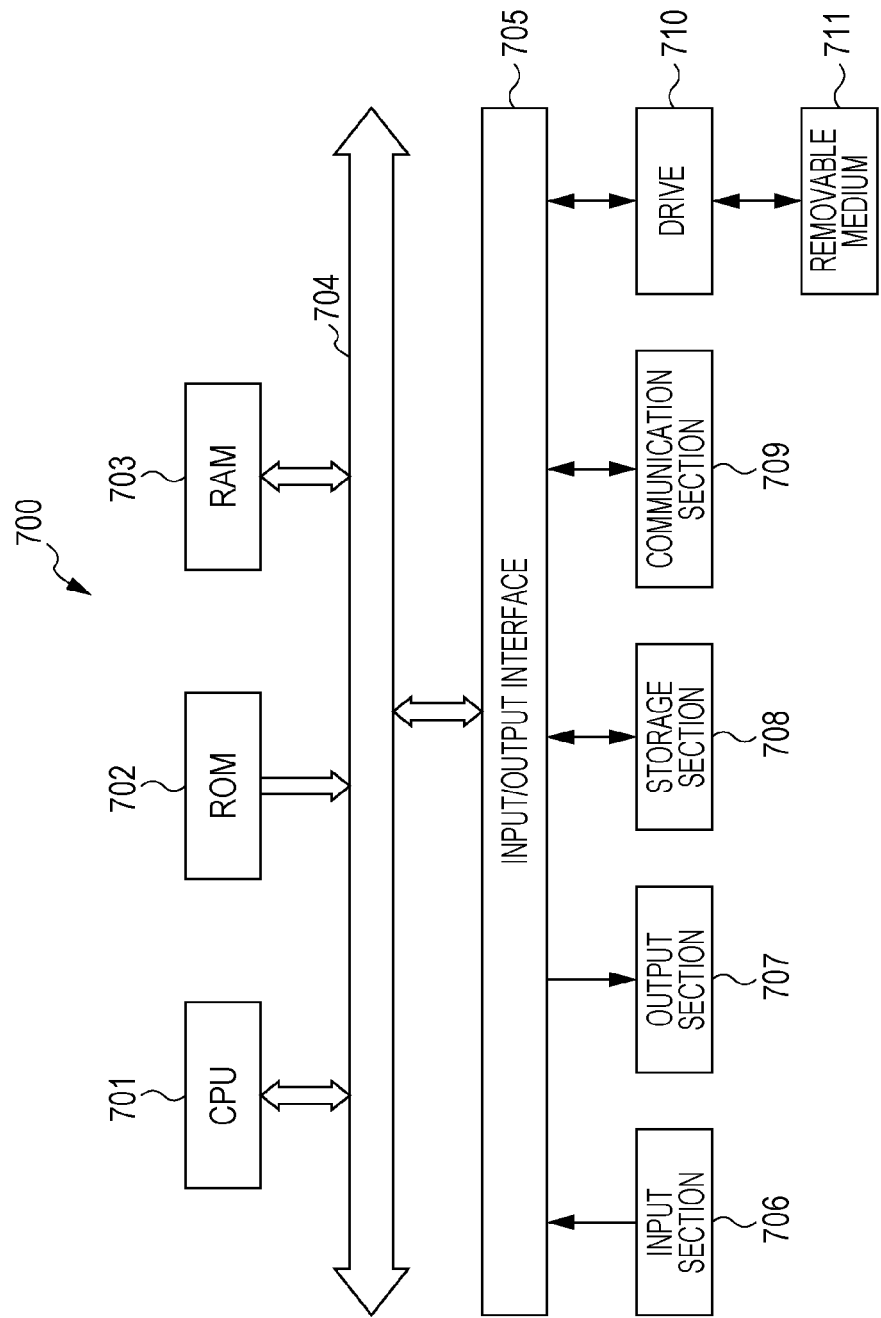
FIG. 16 is a block diagram illustrating an example of a configuration of a personal computer.

In FIG. 16, a CPU (Central Processing Unit) 701 performs various kinds of processing in accordance with the program stored in a ROM (Read Only Memory) 702 or the program loaded into a RAM (Random Access Memory) 703 from a storage section 708. Also, the RAM 703 suitably stores data necessary for executing various kinds of processing performed by the CPU 701, etc.

The CPU 701, the ROM 702, and the RAM 703 are mutually connected through a bus 704. An input/output interface 705 is also connected to the bus 704.

An input section 706 including a keyboard, a mouse, etc., an output section 707 including a display including an LCD (Liquid Crystal Display) etc., and a speaker, etc., are connected to the input/output interface 705. Also, a storage section 708 including a hard disk, etc., a communication section 709 including a modem, a network interface card, such as a LAN card, are connected to the input/output interface 705. The communication section 709 performs communication processing through a network including the Internet.

A drive 710 is connected to the input/output interface 705 as necessary. A removable medium 711, such as a magnetic disk, an optical disc, a magneto-optical disc, or a semiconductor memory, etc., are suitably attached to the drive 710, and computer programs read the removable media are installed into the storage section 708 as necessary.

If the above-described series of processing is performed by software, the programs constituting the software are installed from a network, such as the Internet, or a recording medium including the removable medium 711.

In this regard, the recording medium includes not only a removable medium 711, which stores the program to be distributed to a user separately from the apparatus main unit, as shown in FIG. 16, including, for example, a magnetic disk (including a floppy disk (registered trademark)), an optical disc (a CD-ROM (Compact Disc-Read Only Memory)), a DVD (Digital Versatile Disc), a magneto-optical disc (including a MD (Mini Disc)(registered trademark)), or a semiconductor memory, etc., but also includes a ROM 702, a hard disk included in a storage section 708, whish stores the program in a state of being incorporated in the apparatus main unit in advance, etc.

In this regard, a series of processing described above in this specification includes, of course, the processing performed in time series in accordance with the described sequence, but also includes the processing that is not necessarily performed in time series, namely, the processing to be performed in parallel or individually.

Also, an embodiment is not limited to the above-described embodiment. It is possible to make various changes without departing from the gist of the present application.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A muscle-activity diagnosis apparatus comprising:
   an acquiring section configured to electrically detect an original myoelectric signal from a test subject;
   a transformed-signal generating section configured to generate a transformed signal by performing Hilbert transformation and inverse Fourier transformation on the original myoelectric signal;
   a phase-velocity calculating section configured to calculate a phase velocity of the myoelectric signal on the basis of phases of the original myoelectric signal and of the transformed signal; and
   a state-identifying section configured to identify an activity state of a muscle of a predetermined part of a body of the test subject for each of the unit time on the basis of a plurality of feature quantities of a waveform of the myoelectric signal in a unit time and the plurality of feature quantities including at least a size of amplitude of the myoelectric signal and the calculated phase velocity.

2. The muscle-activity diagnosis apparatus according to claim 1,
   wherein the acquiring section is configured to differentially detect an electronic signal obtained from an earphone sensor inserted into an external auditory canal of the test subject, and digitize the signal so as to obtain the myoelectric signal.

3. The muscle-activity diagnosis apparatus according to claim 2,
   wherein the state-identifying section is configured to identify activity states of muscles of a plurality of parts of a face of the test subject, and outputs a signal indicating a facial expression of the test subject estimated on the basis of the identified activity states of the muscles of the plurality of parts.

4. The muscle-activity diagnosis apparatus according to claim 2,
   wherein the earphone sensor is provided with
   a myoelectric electrode for detecting an electronic signal generated by muscle activity of the test subject;
   a voltage detection electrode for detecting a reference voltage being a difference between a potential in an ear of the test subject and a potential of a circuit in the earphone sensor; and
   a feedback electrode for supplying a feedback voltage generated by inversely amplifying the reference voltage.

5. The muscle-activity diagnosis apparatus according to claim 1,
   wherein using the plurality of feature quantities of the waveform of the myoelectric signal in the unit time provided in advance as parameters, the state-identifying section is configured to perform machine learning on the basis of a sample having a corresponding relationship between the parameter and the activity state of the muscle of the test subject, and is configured to identify the plurality of feature quantities of the myoelectric signal on the basis of a result of the machine learning so as to identify the activity state of the muscle of the predetermined part of the body of the test subject.

6. The muscle-activity diagnosis apparatus according to claim 5,
   wherein AdaBoost is used as the identification method by the machine learning.

7. A method of diagnosing muscle activity, the method comprising:
   electrically detecting an original myoelectric signal from a test subject;
   generating a transformed signal by performing Hilbert transformation and inverse Fourier transformation on the original myoelectric signal;
   calculating a phase velocity of the myoelectric signal on the basis of phases of the original myoelectric signal and the transformed signal; and
   identifying an activity state of a muscle of a predetermined part of a body of the test subject for each of the unit time on the basis of a plurality of feature quantities of a waveform of the myoelectric signal in a unit time and the plurality of feature quantities including at least a size of amplitude of the myoelectric signal and the calculated phase velocity.

8. A computer program product stored on a non-transitory computer readable medium for causing a computer to function as a muscle-activity diagnosis apparatus, the apparatus comprising:
- an acquiring section configured to electrically detect an original myoelectric signal from a test subject;
- a transformed-signal generating section configured to generate a transformed signal by performing Hilbert transformation and inverse Fourier transformation on the original myoelectric signal;
- a phase-velocity calculating section configured to calculate a phase velocity of the myoelectric signal on the basis of phases of the original myoelectric signal and the transformed signal; and
- a state-identifying section configured to identify an activity state of a muscle of a predetermined part of a body of the test subject for each of the unit time on the basis of a plurality of feature quantities of a waveform of the myoelectric signal in a unit time and the plurality of feature quantities including at least a size of amplitude of the myoelectric signal and the calculated phase velocity.

* * * * *